United States Patent
Kates et al.

(10) Patent No.: US 6,968,327 B1
(45) Date of Patent: Nov. 22, 2005

(54) METHOD FOR TRAINING A NEURAL NETWORK

(76) Inventors: Ronald Kates, Palnkamer Strasse 49, 83624 Otterfing (DE); Nadia Harbeck, Palnkamer Strasse 49, 83624 Otterfing (DE); Manfred Schmitt, Hohenaschauer Strasse 10, 81669 Munchen (DE)

( * ) Notice: Subject to any disclaimer, the term of this patent is extended or adjusted under 35 U.S.C. 154(b) by 157 days.

(21) Appl. No.: 10/049,650

(22) PCT Filed: Aug. 24, 2000

(86) PCT No.: PCT/EP00/08280

§ 371 (c)(1),
(2), (4) Date: May 2, 2002

(87) PCT Pub. No.: WO01/15078

PCT Pub. Date: Mar. 1, 2001

(30) Foreign Application Priority Data

Aug. 26, 1999 (DE) .................. 199 40 577

(51) Int. Cl.[7] .................. G06E 1/00; G06E 3/00; G06F 15/18; G06G 7/00
(52) U.S. Cl. .................. 706/21; 706/15; 706/16
(58) Field of Search .................. 706/21, 15, 16

(56) References Cited

U.S. PATENT DOCUMENTS

| | | | | |
|---|---|---|---|---|
| 5,528,700 A | * | 6/1996 | Takatori et al. | 382/157 |
| 5,687,286 A | * | 11/1997 | Bar-Yam | 704/232 |
| 5,734,797 A | * | 3/1998 | Deangelis et al. | 706/15 |
| 5,812,992 A | | 9/1998 | de Vries | |
| 6,594,629 B1 | * | 7/2003 | Basu et al. | 704/251 |
| 6,601,051 B1 | * | 7/2003 | Lo et al. | 706/23 |

OTHER PUBLICATIONS

Kishan Mehrotra et al, Artificial Neural Networks, 1997, MIT Press, 1, 19, 116, 117, 118.*
Kishan Mehrotra et al, Elements of Artificial Neural Networks, 1997, MIT Press, 8, 10, 11 and 46.*

* cited by examiner

*Primary Examiner*—Joseph P. Hirl
(74) *Attorney, Agent, or Firm*—IP Strategies

(57) ABSTRACT

A method for training a neural network in order to optimize the structure of the neural network includes identifying and eliminating synapses that have no significant influence on the curve of the risk function. First and second sending neurons are selected that are connected to the same receiving neuron by respective first and second synapses. It is assumed that there is a correlation of response signals from the first and second sending neurons to the same receiving neuron. The first synapse is interrupted and a weight of the second synapse is adapted in its place. The output signals of the changed neural network are compared with the output signals of the unchanged neural network. If the comparison result does not exceed a predetermined level, the first synapse is eliminated, thereby simplifying the structure of the neural network.

14 Claims, 1 Drawing Sheet

METHOD FOR TRAINING A NEURAL NETWORK

1. FIELD OF THE INVENTION

Figure 1:
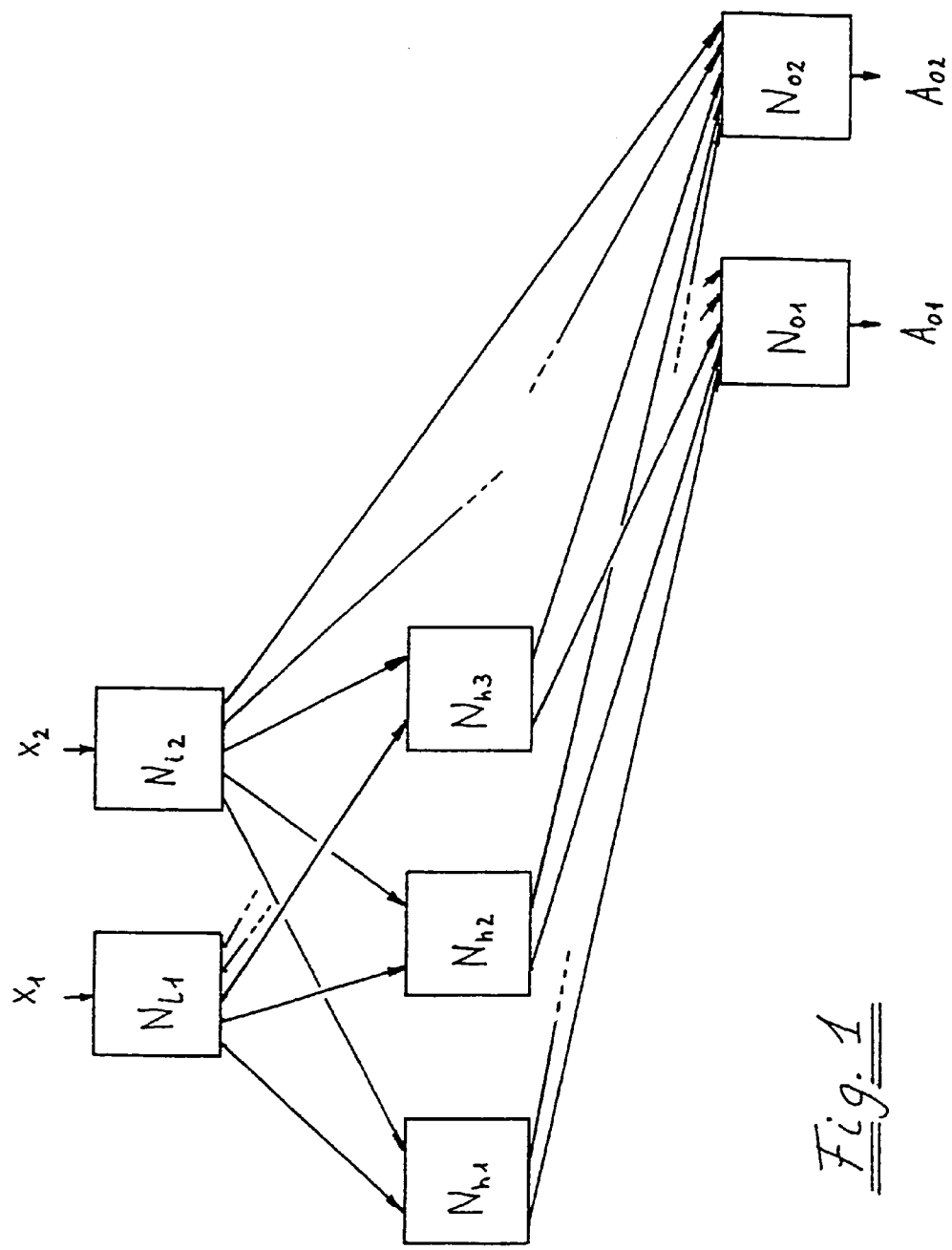

The invention relates to a method for training a neural network to determine risk functions for patients following a first occurrence of a predetermined disease on the basis of given training data records containing objectifiable and for the most part metrologically captured data relating to the medical condition of the patient, wherein the neural network comprises an input layer having a plurality of input neurons and at least one intermediate layer having a plurality of intermediate neurons, as well as an output layer having a plurality of output neurons, and a multiplicity of synapses which interconnect two neurons of different layers in each case.

2. BACKGROUND ART

2.1. General

For large scale data analysis, neural networks have supplemented or replaced hitherto conventional methods of analysis in many fields. It has namely been shown that neural networks are better than conventional methods at discovering and identifying in the datasets hidden, not immediately evident dependencies between individual input data. When new data of the same data type is input, neural networks which have been trained using a known dataset therefore deliver more reliable results than previous methods of analysis.

In the field of medical applications for example, the use of neural networks to determine a survival function for patients suffering from a particular disease, such as cancer, is known. Said survival function indicates the probability of a predetermined event occurring for the patient in question depending on the time that has elapsed since the first occurrence of the disease. Said predetermined event need not necessarily be the death of the patient, as would be inferred from the designation "survival function", but may be any event, for example a recurrence of cancer.

The data records comprise a whole range of objectifiable information, that is to say data on whose value any neural network operator has no influence and whose value can be automatically captured if desired. In the case of breast cancer this is information about the patient's personal data, such as age, sex and the like, information about the medical condition, such as number of lymph nodes affected by cancer, biological tumor factors such as upA (Urokinase Plasminogen Activator), its inhibitor PAI-1 and similar factors, as well as information about the treatment method, for example type, duration and intensity of chemotherapy or radiotherapy. It goes without saying that a whole range of the abovementioned information, in particular the information about the medical condition, can only be determined using suitable measuring apparatus. Furthermore, the personal data can be automatically read in from suitable data media, for example machine-readable identity cards or the like. If they are not all available at the same time, which is often the case especially with laboratory measurements, the objectifiable data can of course be temporarily stored in a database on a suitable storage medium before they are fed to the neural network as input data.

2.2. The Neural Network as Signal Filter

In accordance with the foregoing, therefore, it is possible to conceive of a neural network as a kind of "signal filter" that filters out a meaningful output signal from a noisy, and therefore as yet non-meaningful input signal. As with any filter, whether or how well the filter is able to fulfill its function depends on whether it is possible to keep the intensity of the filter's intrinsic noise low enough that the signal to be filtered out is not lost in this intrinsic noise.

The greater the number of data records available for training the neural network on the one hand and the simpler the structure of the neural network on the other hand, the lower the intensity of the "intrinsic noise" of a neural network. Moreover, the generalizability of the network increases, the simpler the structure of the neural network. In the case of a conventional procedure in the prior art, therefore, one part of the training of neural networks is concerned with locating and eliminating parts of the structure that can be dispensed with for obtaining a meaningful output signal. With this "thinning out" (also known as "pruning" in the jargon) however, a further constraint to be taken into account is that the structure of the neural network cannot be "pruned" ad infinitum because as the complexity of the neural network is reduced, its ability to map complex interrelationships, and hence its meaningfulness, is also diminished.

2.3. Problems with Medical Application

In practice, and in particular in the case of the medical application of neural networks mentioned at the beginning, the problem is often encountered that only very small datasets of typically a few hundred data records are available for training the neural network. To compound the difficulty, not only a training dataset, but also a validation dataset and a generalization dataset must be provided for the training. The significance of said two datasets will be discussed in greater detail below in sections 5.5 and 5.7.

With such small datasets, the use of known pruning methods always led to so great a simplification of the structure of the neural network that the meaningfulness of the neural network diminished to an unacceptable level. To nevertheless obtain neural networks that delivered meaningful output signals after completion of the training phase, in the prior art neural networks with a rigid, that is to say fixed and invariable, structure were used where only small training datasets were available. The degree of complexity, or the simplicity, of this rigid structure was selected here on the basis of empirical knowledge in such a way that the neural network had on the one hand a high degree of meaningfulness while on the other hand having a still acceptable intrinsic noise level. It has hitherto been assumed that the specification of an invariable structure was unavoidable.

Another problem with medical applications of neural networks is the fact that only "censored" data are available for training. The term "censored" is used to denote the circumstance that it is not possible to foresee the future development for patients who have fortunately not yet suffered a relapse at the time of data capture, and statements about the survival function are therefore only possible up until the time the data were recorded.

It goes without saying that in particular in the case of medical applications it is not possible to forego a truly meaningful result under any circumstances whatsoever. Under no circumstances is it namely acceptable for even one single patient to be denied a treatment simply because the neural network did not consider it necessary. The consequences for the patient could be incalculable.

With respect to the details of the prior art outlined above, please see the articles listed in section 6. "References".

3. BRIEF SUMMARY OF THE INVENTION

In the light of the above, the object of the invention is to provide an automatic method for training a neural network to determine risk functions for patients following a first occurrence of a predetermined disease, which method permits, despite a low number of available training data records, the use of a neural network having a variable structure and the optimization of its structure in at least one structure simplification step.

According to the invention, this object is achieved by a method for training a neural network to determine risk functions for patients following a first occurrence of a predetermined disease on the basis of given training data records containing objectifiable and metrologically captured data relating to the medical condition of the patient, wherein the neural network comprises:

an input layer having a plurality of input neurons,
at least one intermediate layer having a plurality of intermediate neurons,
an output layer having a plurality of output neurons, and
a multiplicity of synapses which interconnect two neurons of different layers in each case, wherein the training of the neural network comprises a structure simplification procedure, that is to say the location and elimination of synapses that have no significant influence on the curve of the risk function, in that one either a1) selects two sending neurons that are connected to one and the same receiving neuron,
a2) assumes that the signals output from said sending neurons to the receiving neuron essentially exhibit the same qualitative behavior, that is to say are correlated to one another,
a3) interrupts the synapse of one of the two sending neurons to the receiving neuron and instead adapts accordingly the weight of the synapse of the respective other sending neuron to the receiving neuron,
a4) compares the reaction of the neural network changed in accordance with step a3) with the reaction of the unchanged neural network, and
a5) if the variation of the reaction does not exceed a predetermined level, decides to keep the change made in step a3), or in that one
b1) selects a synapse,
b2) assumes that said synapse does not have a significant influence on the curve of the risk function,
b3) interrupts said synapse,
b4) compares the reaction of the neural network changed in accordance with step b3) with the reaction of the unchanged neural network, and
b5) if the variation of the reaction does not exceed a predetermined level, decides to keep the change made in step b3).

A neural network trained in the manner described above assists the attending physician for example when deciding on the follow-up treatment for a particular newly operated patient. For this the physician can input into the neural network the patient data and the data metrologically captured in the laboratory relating to the medical condition of the first treatment, and receives from the neural network information about what type of follow-up treatment would produce the most favorable survival function for the patient in question. It is of course also possible to take account of the aggressiveness of the individual types of follow-up treatment so that, given an equally favorable or virtually equally favorable survival function, the least aggressive follow-up treatment for the patient can be selected.

4. BRIEF DESCRIPTION OF THE DRAWING

FIG. 1 is a diagram of the structure of a neural network constructed in the manner of a multi-layer perceptron.

5. DETAILED DESCRIPTION OF THE INVENTION

The invention is explained in greater detail below with reference to an exemplary embodiment.

5.1. Structure of Neural Networks

FIG. 1 shows the structure of a neural network which is constructed in the manner of a multi-layer perceptron. In this case the neural network comprises:

an input layer having a plurality of input neurons $N_i$ (i for "input neuron"),
at least one intermediate layer having a plurality of intermediate neurons $N_h$ (h for "hidden neuron"),
an output layer having a plurality of output neurons $N_o$ (o for "output neuron"), and
a multiplicity of synapses which interconnect two neurons of different layers in each case.

In the simplified embodiment according to FIG. 1, on which the following discussion will be based for the sake of clarity, only a single intermediate layer is provided, and the neurons (or nodes as they are also frequently called) of the output layer are connected via synapses (also called "connectors") to both each neuron of the input layer and to each neuron of the intermediate layer.

The number of input neurons is usually chosen depending on the number of objectifiable items of information available. However, if the time required for determining the reaction of the neural network should consequently rise to an unacceptable level, then it is possible, for example with the aid of neural networks having a greatly simplified structure, to make a preliminary estimation of the significance of the individual objectifiable items of information for the meaningfulness of the overall system. It should however be stressed that this preliminary estimate is also performed automatically and without the intervention of the respective operator. Furthermore, the number of output neurons is chosen to be large enough that, for the purposes of a series expansion of the survival function, a sufficient number of series expansion terms are available to achieve a meaningful approximation to the actual survival function. Finally, the number of intermediate neurons is chosen to be large enough that the results of the trained neural network are meaningful, but small enough that the time required to determine the result is acceptable.

5.2. Function of Neural Networks 5.2.1. General

Each neuron receives a stimulation signal S, processes it in accordance with a predetermined activation function F(S) and outputs a corresponding response signal A=F(S) which is fed to all neurons located below said neuron. The stimulation signal $S_y$ that acts on the neuron NY in question is usually formed by summing the response signals $A_x$ of the neurons $N_x$ located above said neuron $N_y$, with the contributions of the individual neurons $N_x$ in each case being factored with a weighting factor $w_{xy}$ that states the strength of the synapse connecting the two neurons into the sum.

Stimulation signal: $S_y = \Box_x w_{xy} \cdot A_x$

Response signal: $A_y = F(S_y)$

5.2.2. Input Layer

The stimulation signals $S_i$ of the input neurons $N_i$ are formed by the input data $x_{i,j}$ relating to a particular patient j.

Stimulation signal: $S_i = x_{i,j}$

In order to be able to interpret the weights of the synapses of a neural network appropriately, it is preferable to work with variables whose values are of the magnitude of 1. To achieve this despite the usually very different distributions of input data, it is customary to subject the input data to an appropriate transformation. Said transformation is performed by the activation function $F_i$ of the input neurons:

Response signal: $A_i = \tanh[(S_i - S_{i,mean})/S_{i,Q}]$

For the input data $x_{i,j}$, therefore, firstly the mean value $S_{i,mean}$ of the patients j belonging to the training dataset is formed. Secondly a scaling factor $S_{i,Q}$ is formed. If the value of an input variable $x_{i,j}$ is above the mean $S_{i,mean}$, then scaling is performed in accordance with the 75% quartile. If, on the contrary, it is below the mean value, then scaling is performed in accordance with the 25% quartile. Finally, by using the hyperbolic tangent function as the activation function $F_i$, scaled response signals with values in the range between −1 and +1 are readily obtained.

Note that the above transformation can be omitted for input data that already exhibit the desired distribution, categorical values or binary values.

5.2.3. Intermediate Layer

The stimulation signal $S_h$ for the neurons $N_h$ of the intermediate layer is formed by the weighted sum of the response signals $A_i$ of all neurons $N_i$ of the input layer:

Stimulation signal: $S_h = \Box_i w_{ih} \cdot A_i$

Said stimulation signal $S_h$ is transformed by the neurons $N_h$ in accordance with a given activation function $F_h$, which may again be the hyperbolic tangent function for example, into a response signal $A_h$:

Response signal: $A_h = F_h(S_h - b_h)$

In the field of neural networks, the parameters $b_h$ are referred to as the "bias" of the respective neuron. Like the values of the synapse weights $w_{xy}$, the values of said bias parameters $b_h$ are also determined during training of the neural network.

5.2.4. Output Layer

The stimulation signal $S_o$ and the response signal $A_o$ for a neuron $N_o$ of the output layer are determined analogously:

Stimulation signal: $S_o = \Sigma_i w_{io} \cdot (A_i - c_i) + \Sigma_h w_{ho} \cdot A_h$ Response signal: $A_o = F_o(S_o - b_o)$ The parameters $b_o$ again indicate the "bias" of the neurons $N_o$ of the output layer, while the parameters $c_i$ serve to adapt the stimulation contributions of the neurons $N_i$ of the input layer and $N_h$ of the intermediate layer. The values of both the parameters $b_o$ and the parameters $c_i$ are determined during the training phase of the neural network. With respect to the bias values $b_o$, it may be favorable to require as a constraint that the response of all output neurons $N_o$ averaged across the complete training dataset is zero. The identity function $F_o(x) = x$ can be used as the activation function $F_o$ for most applications, in particular for the present case where the survival function is being determined for cancer patients.

The response signals $A_o$ of the output neurons $N_o$ indicate the respective coefficients of the associated terms of the series expansion of the survival function sought.

5.3. The Survival Function

As already mentioned above, the input data comprise information about the patient's personal data as well as information about the medical condition. All these data are captured at a time t=0, in the case of cancer patients the time of the first operation for example. Following the first operation, the patients then undergo a particular follow-up treatment, which may include chemotherapy and/or radiotherapy for example.

The survival function S(t) indicates for a patient in question at a time t the probability that a particular event has not yet occurred. Said particular event may be, for example, a recurrence of cancer, or also in the worst case the death of the patient. In any case, S(0)=1 holds for the survival function. In addition, S(∞)=1 is usually assumed.

According to conventional notation, it is possible to define an event density f(t) and a risk function λ(t) on the basis of the survival function S(t):

$f(t) = -dS/dt$ $\lambda(t) = f(t)/S(t)$ from which it follows that:

$\lambda(t) = -(d/dt)[\ln S(t)]$

If one knows the curve of the risk function λ(t) therefore, it is possible to reconstruct the curve of the survival function S(t) by means of integration.

The task of the neural network is to model the curve of the risk function λ(t) in the same way as a series expansion:

$\lambda(t) = \lambda_o \cdot \exp[\Sigma_o B_o(t) \cdot A_o]$

According to the above notation, the parameters $A_o$ denote the response signals of the neurons $N_o$ of the output layer of the neural network. In the context of the present invention, $\lambda_o$ is a parameter independent of t which is used as a scaling factor. $B_o(t)$ denotes a set of functions that, as base functions of the series expansion, enable a good approximation to the actual curve of the risk function. It is possible to use for example the fractal polynomials or else functions such as $t^p$ (where p is not necessarily an integer) as the function set $B_o(t)$. $B_{o1}(t) = 1$; $B_{o2}(t) = \text{const} \cdot t^{1/2}$, ... were used for the present invention.

5.4. Training of the Neural Network—Preparations

5.4.1. The Optimization Function

The training dataset comprises the data records of a plurality of patients for whom not only personal data and information about the medical condition, but also information about the type of follow-up treatment and the further progress of the disease are known. From the collected data relating to the further progress of the disease, an "actual survival function" is constructed according to the following rules: if the predetermined event, for example a relapse or the death of the patient, has already occurred for a particular patient at a time t, then his contribution δ to the "actual survival function" is set to δ=0 before time t and to δ=1 at time t and after time t. Patients for whom the predetermined event has not yet occurred at the time the training dataset was created ("censored" data) contribute only δ=0 to the "actual survival function" at all times. During the training phase the weights $w_{xy}$ of the synapses and the other optimization parameters set out in section 5.2. above are then set in such a way that the survival function delivered by the neural network optimally matches the "actual survival function".

This can be achieved, for example, by defining a suitable optimization function O for this purpose and searching for a local, in the most favorable case even the global, minimum of said optimization function in the space covered by the optimization parameters. To define the optimization function O, it is already known in the prior art to start from a so-called likelihood function L:

$$O = -\ln L$$

According to the invention $$L = \Pi_j [f_j(t)]^{\delta} \cdot [S_j(t)]^{1-\delta}$$

is chosen to represent the likelihood function where, in accordance with the notation introduced in section 5.3., $f_j(t)$ and $S_j(t)$ denote the event density and the survival function for the patient j of the training set. Said likelihood function has the advantage that the computational effort rises only approximately proportionately to the number of patients included in the training dataset.

Another way of representing the likelihood function is:

$$L = \Pi_j < \exp[\Box_o B_o(t) \cdot A_{oj}] \; \Pi \Box_l \exp[\Box_{li \; Bo}(t) \cdot A_{ol}] >$$

where the product is formed across all patients j for whom the predetermined event has already occurred at time t, and where the first sum in the denominator of the quotient is formed across all patients l for whom the predetermined event has not yet occurred at time t.

The computational effort associated with this representation does however rise approximately proportionately to the square of the number of patients included in the training dataset.

5.4.2. The Initialization

As is known per se in the prior art, to initialize the network optimization parameters, for example the weights of the synapses connecting the neurons, it is possible to assign stochastically to said parameters small values that conform to certain normalization rules. It is additionally possible here to include in the normalization findings obtained in preliminary test runs on neural networks having a greatly simplified structure.

5.5. Training the Neural Network—Simplex Method

As is customary, the search for a local or the global minimum of the optimization function is performed in several steps or cycles. According to the invention, however, for the first time the simplex method proposed by Nelder and Mead (see section 6. "References") is used in a neural network for this search. A simplex is an (n+1)-dimensional structure in an n-dimensional space which surrounds the current basepoint in the n-dimensional space, i.e. a triangle in 2-dimensional space, a tetrahedron in a 3-dimensional space and so forth. In what directions and at what distances from the current basepoint the (n+1) vertices are arranged is determined here from the vertices of the preceding cycle on the basis of the characteristics of the optimization function.

This method leads to a strictly monotonic decreasing sequence of basepoints. It can be continued until either (within given precision limits) a local or global minimum has been identified or another termination criterion has been fulfilled. In connection with said further termination criterion, the abovementioned validation dataset now comes into play:

The abovementioned monotonic decrease in basepoints can arise on the one hand from actually objectifiable characteristics of the optimization function specified for the training dataset. On the other hand, it is also possible that the decrease occurs in the range of a valley of the optimization function caused by stochastic fluctuations. The latter effect however only simulates a learning success. For this reason, according to the invention the characteristics of the optimization function specified on the basis of the validation dataset are also investigated at the same basepoints. If it is then determined that the basepoints of the "validation data optimization function" also exhibit a monotonic decrease, then it can be assumed that one is still in a "true" learning phase of the neural network. If on the other hand the sequence of basepoints of the "validation data optimization function" stagnates, or if it even rises again, it must be assumed that with respect to the "training data optimization function" one is in a valley caused by stochastic fluctuations which only simulates a learning progress. The cyclical execution of the simplex method can therefore be interrupted.

The main advantage of the simplex method is that it can be performed solely on the basis of the optimization function, and also that the step length and step direction can be automatically specified.

5.6. Training the Neural Network—Structure Simplification ("Pruning")

Once the search for a local or the global minimum has been completed, the next training step is to investigate whether it is possible to simplify the structure of the neural network on the basis of the findings so far. This "pruning" is concerned with investigating which of the synapses have so little influence on the overall function of the neural network that they can be omitted. In the simplest case this can be, for example, permanently setting the weight assigned to them to zero. However, in principle it is equally conceivable to "freeze" the weight of the respective synapse to a fixed value. It is advantageous to alternate between simplex optimization steps and structure simplification steps in an iterative process. It would of course be desirable for the neural network to undergo a new simplex optimization after a single synapse has been excluded. In view of the total time required for training however, this is unjustifiable. In practice a favorable compromise has proved to be the removal during a structure simplification step of at most 10% of the synapses still present at the beginning of said step.

According to the invention the two methods described below in sections 5.6.1. and 5.6.2. are used for structure simplification.

5.6.1. Likelihood Method

With this method the value of the likelihood function is first calculated as a reference value on the basis of the complete structure of the neural network in its present state of training, i.e. using the current values of the weights of all synapses. Following this, the influence of a given synapse is suppressed, i.e. the value of the weight of this synapse is set to zero. The value of the likelihood function is then calculated for the thus simplified network structure, and the ratio of this value to the reference value is formed.

Once said likelihood ratio has been calculated for all synapses, when performing the steps described below, a start is made with the synapse for which the value of the likelihood ratio is nearest to one:

Assuming that the network structure has already been simplified by (x−1) synapses and the significance of the xth synapse is now being investigated, then the following three network structure variants are compared: firstly the complete structure of the neural network in its current state of training with all synapses still present prior to this structure simplification state, secondly the network structure excluding the $(x-1)$ synapses already suppressed in this structure simplification step, and thirdly the network structure now also excluding the xth synapse. Following this, using a significance test the third structure variant is compared firstly with the first structure variant (complete structure) and secondly with the second structure variant $((x-1)$ synapses suppressed). If even just one of the two tests produces too great a deviation from the third structure variant, then the respective synapse is retained at least for the next simplex optimization step.

The CHI-SQUARED test (cf. section 6. "References", Document . . . ) which is known per se can be used as a significance test for example. Alternatively, said significance test could also be performed using the BOOT-STRAPPING method (cf. section 6. "References", Document . . . ) which is likewise known per se. The use of the CHI-SQUARED test is particularly favorable if the reaction of the neural network is determined on the basis of a likelihood function. The BOOT-STRAPPING method is also suitable with other types of functions for representing the reaction of the neural network.

5.6.2. Correlation Method

The exclusion or suppression of synapses according to the correlation method is based on the consideration that it could be possible for two neurons located on one and the same layer to have qualitatively the same influence on one neuron on a lower layer. In this case the reaction of the neural network, or to be more precise the response signal of said latter neuron, should not change significantly if said neuron is stimulated by only one of the two neurons located above it, and the influence of the second neuron is taken into account by strengthening the remaining synapse. It would then be possible to omit the synapse leading from the second neuron to the neuron in question.

a. Synapses Connecting Input Neurons and Output Neurons

In accordance with section 5.2.4., the contribution of the response signal of two input neurons to the stimulation signal of an output neuron takes the form:

$$S_o = w_{1o}(A_1 - c_1) + w_{2o}(A_2 - c_2)$$

If one then assumes that the two response signals $A_1$ and $A_2$ are correlated at least approximately to one another in accordance with $$A_2 = m \cdot A_1 + n$$

and that the weight $w_{1o}$ is greater than the weight $W_{2o}$, then the following holds for the stimulation signal $S_o$:

$$S_o = (w_{1o} + w_{2o} \cdot m) \cdot A_1 + (n \cdot w_{2o} - w_{1o} \cdot c_1 - w_{2o} \cdot c_2)$$

$$= w^*_{1o} \cdot (A_1 - c^*_1)$$

where $$w^*_{1o} = W_{1o} + w_{2o} \cdot m$$

and $$c^*_1 = -[(n \cdot w_{2o} - w_{1o} \cdot c_1 - w_{2o} \cdot c_2)] / (w_{1o} + w_{2o} \cdot m)$$

If $w^*_{1o}$ is non-small, the behavior of the neural network can be tested with the following assumptions:
1. Replace the weight $w_{1o}$ by $w^*_{1o}$;
2. Replace the parameter $c_1$ by $c^*_1$; and
3. Suppress the synapse from the input neuron $N_2$ to the output neuron $N_o$.

If the outcome of this test, which can again be performed as a CHI-SQUARED test for example, is positive, then it is possible to omit the synapse from the input neuron $N_2$ to the output neuron $N_o$.

b. Synapses Connecting Input Neurons and Intermediate Neurons

The contribution of the response signal of two input neurons to the stimulation signal of an intermediate neuron can also be treated analogously, in which case it is advisable, for reasons that will become immediately apparent below, to treat the stimulation signal of the intermediate neuron including its "bias":

$$S_h - b_h = w_{1h} \cdot A_1 + w_{2h} \cdot A_2$$

If one again assumes that the two response signals $A_1$ and $A_2$ are correlated at least approximately to one another in accordance with $$A_2 = m \cdot A_1 + n$$

and that the weight $W_{1h}$ is greater than the weight $w_{2h}$, then the following holds for the stimulation signal $S_h$:

$$S_h - b_h = (w_{1h} + w_{2h} \cdot m) \cdot A_1 + n \cdot w_{2h}$$

or $$S_h - b^*_h = w^*_{1h} \cdot A_1$$

where $$w^*_{1h} = W_{1h} + w_{2h} \cdot m$$

and $$b^*_h = b_h + n \cdot w_{2h}$$

If $w^*_{1h}$ is non-small, the behavior of the neural network can be tested with the following assumptions:
1. Replace the weight $w_{1h}$ by $w^*_{1h}$;
2. Replace the bias $b_h$ by $b^*_h$; and
3. Suppress the synapse from the input neuron $N_2$ to the intermediate neuron $N_h$.

If the outcome of this test, which can again be performed as a CHI-SQUARED test for example, is positive, then it is possible to omit the synapse from the input neuron $N_2$ to the intermediate neuron $N_h$.

c. Synapses Connecting Intermediate Neurons and Output Neurons

Synapses leading from intermediate neurons to output neurons can also be treated analogously. With respect to the bias values $b_o$, however, the further constraint mentioned in section 5.2.4. may need to be taken into account.

5.6.3. Testing the Topology

The above-described pruning of the structure of the neural network can result in individual neurons no longer being connected to any other neurons. This is the case for example if an input neuron is not connected to any intermediate neuron nor to any output neuron, or if an output neuron is not connected to any intermediate neuron nor to any input neuron. It is therefore only logical to completely deactivate these neurons that no longer have an influence on the function of the neural network.

Intermediate neurons that are still connected to neurons on the input layer but not to neurons on the output layer constitute a special case. Said intermediate neurons can no longer exert any influence on the function of the neural network. The synapses leading from the input layer to these intermediate neurons can therefore also be suppressed, i.e. the weights of said synapses can be set to zero.

The converse case can however also occur, namely that an intermediate neuron is still connected to the output layer, but no longer has any connection to the input layer. At best said intermediate neurons can output to the output neurons a response signal that is dependent on their "bias". However, a signal of this type has no information content whatsoever that would be significant for the function of the neural network. It is therefore also possible to suppress the remaining synapses of said intermediate neurons.

5.7. Generalization

On completion of the training phase it is necessary to test the performance of the trained neural network to obtain a measure of how meaningful the survival functions delivered by this neural network actually are. The abovementioned generalization dataset, which had no influence whatsoever on the training of the neural network and thus enables objective results, is used for this purpose.

5.8. Concluding Remarks

In conclusion it should be mentioned that, in addition to the tumor-specific factors upA and PAI-1 explicitly mentioned above which allow statements to be made about invasion, it is also possible to take further such factors into account. Among others, these include factors for proliferation, for example the S phase and Ki-67, and other processes that influence tumor growth.

6. REFERENCES

Reference is made to the following publications relating to the prior art:
1. Barnhill, S., Zhang, Z., U.S. Pat. No. 5,769,074, 'Computer assisted methods for diagnosing diseases'.
2. Bellotti, M., et al. (1997), 'Neural networks as a prognostic tool for patients with non-small cell carcinoma of the lung', Mod Pathol. December, 10(12), 1221.
3. Biganzoli, E., Boracchi, P., Mariani, L., Marubini, E. (1998), 'Feed Forward Neural Networks for the Analysis of Censored Survival Data: A Partial Logistic Regression Approach', Statistics in Medicine, 17, 1169.
4. Bostwick, D. G. (1998), 'Practical clinical application of predictive factors in prostate cancer: A review with an emphasis on quantitative methods in tissue specimens', Anal Quant Cytol Histol. October, 20(5), 323–42. Review.
5. Bottaci, L. et al. (1997), 'Artificial neural networks applied to outcome prediction for colorectal cancer patients in separate institutions', Lancet. August 16, 350, 469.
6. Bryce, T. J. et al. (1998), 'Artificial neural network model of survival in patients treated with irradiation with and without concurrent chemotherapy for advanced carcinoma of the head and neck', Int J Radiat Oncol Biol Phys. May 1, 41(2), 339.
7. Burke, H. B. et al. (1997), 'Artificial neural networks improve the accuracy of cancer survival prediction', Cancer. February 15, 79(4), 857.
8. Cox, D. (1972), 'Regression Models and Life Tables', J R Stat Soc [B] 34, 187.
9. Comanor, L., Minor, J., U.S. Pat. No. 5,860,917, 'Method and apparatus for predicting therapeutic outcomes'.
10. De Laurentiis, M. & Ravdin, P. (1994), 'Survival Analysis of Censored Data, Neural Network Analysis Detection of Complex Interactions Between Variables', Breast Cancer Res Tr 32, 113.
11. Ebell, M. (1993), 'Artificial Neural Network Model for Predicting Failure to Survive Following In-Hospital Cardiopulmonary Resuscitation', The Journal of Family Practice, 36, 297.
12. Faraggi, D. & Simon, R. (1995), 'A Neural Network Model for Survival Data', Statistics in Medicine, 14, 73.
13. Faraggi, D., Simon, R., Yaskil, E., Kramar A. (1997), 'Bayesian Neural Network Models for Censored Data', Biometrical Journal, 39, 519.
14. Fogel, D., Wasson, E. & Boughton, E. (1995), 'Evolving Neural Networks for Detecting Breast Cancer', Cancer Letters, 96, 49.
15. Gray, R. (1992), 'Flexible Methods for Analyzing Survival Data Using Splines, with Applications to Breast Cancer Prognosis', J. American Statistical Association, 87, 942.
16. Hamamoto, I. et al. (1995), 'Prediction of the early prognosis of the hepatectomized patient with hepatocellular carcinoma with a neural network', Comput Biol Med. January, 25(1), 49.
17. Hastie, T., Sleeper, L. & Tibshirani, R. (1992), 'Flexible Covariate Effects in the Proportional Hazards Model', Breast Cancer Res Tr 22, 241.
18. Hilsenbeck, S. & Clark, G. (1996), 'Practical p-Value Adjustment for Optimally Selected Cutpoints', Statistics in Medicine, 15, 103.
19. Hilsenbeck, S., Clark, G. & McGuire, W. (1992), 'Why Do So Many Prognostic Factors Fail to Pan Out?', Breast Cancer Res Tr 22, 197.
20. Jefferson, M. F. et al. (1997), 'Comparison of a genetic algorithm neural network with logistic regression for predicting outcome after surgery for patients with nonsmall cell lung carcinoma', Cancer. April 1, 79(7), 1338.
21. Kalbfleisch, J. & Prentice, R. (1980), *The Statistical Analysis of Failure Time Data*, Wiley.
22. Kappen, H. J. et al. (1993), 'Advanced ovarian cancer: Neural network analysis to predict treatment outcome', Ann Oncol., 4 Suppl 4, 31.
23. Kharchenko E. P. (1996), '[The use of a neural network model for cancer prognosis on the basis of immunological indices]', Biull Eksp Biol Med. August, 122(8), 206. Russian.
24. Knorr, K., Hilsenbeck, S., Wenger, C. et al. (1992), 'Making the Most of Your Prognostic Factors, Presenting a More Accurate Survival Model for Breast Cancer Patients', Breast Cancer Res Tr 22, 251.
25. Koutsoukous, A. D. et al. (1994), 'Discrimination techniques applied to the NCI in vitro anti-tumour drug screen: predicting biochemical mechanism of action', Stat Med. March 15–April 15, 13(5–7), 719.
26. Le Cun, Y., Denker, J., Solla, S. (1990), 'Optimal Brain Damage' in Advances in Neural Information Processing Systems 2, (ed. D. Touretzky), San Mateo.
27. Liestol, K., Anderson, P. & Anderson, U. (1994), 'Survival Analysis and Neural Nets', Statistics in Medicine, 13, 1189.
28. Mariani, L. et al. (1997), 'Prognostic factors for metachronous contralateral breast cancer, a comparison of the linear Cox regression model and its artificial neural network extension', Breast Cancer Res Treat. June, 44(2), 167.
29. Marsh, J. W. et al. (1998), 'Liver transplantation in the treatment of hepatocellular carcinoma', J Hepatobiliary Pancreat Surg. 5(1), 24.
30. Marsh, J. W. et al. (1997), 'The prediction of risk of recurrence and time to recurrence of hepatocellular carcinoma after orthotopic liver transplantation, a pilot study. Hepatology. August, 26(2), 444.
31. McGuire, W. L. et al. (1992), 'Treatment decisions in axillary node-negative breast cancer patients', J Natl Cancer Inst Monogr., (11), 173.
32. McGuire, W., Tandon, A., Allred, D., Chamness, G. & Clark, G. (1990), 'How To Use Prognostic Factors in Axillary Node-Negative Breast Cancer Patients', J. Natl Canc Inst 82, 1006.
33. Naguib, R. N. et al (1198), 'Neural network analysis of combined conventional and experimental prognostic markers in prostate cancer: a pilot study', Br J Cancer. July, 78(2), 246.
34. Naguib, R. N. et al. (1997), 'Prediction of nodal metastasis and prognosis in breast cancer: a neural model', Anticancer Res. July–August, 17(4A), 2735.
35. Nelder, J. A. & Mead, R. (1965), 'A simplex method for function minimization', Computer Journal 7, 308.
36. Nowlan, S. J. (1991), *Soft Competitive Adaption, Neural Network Learning Algorithms based on Fitting Statistical Mixtures*, PhD Thesis, School of Comp. Sc., Carnegie Mellon, Pittsburgh.
37. Press, W., Teukolsky, S., Flannery, B. & Vetterling, W. (1992), *Numerical Recipies, The Art of Scientific Computing*, Cambridge.
38. Ravdin, P. & Clark, G. (1992), 'A Practical Application of Neural Network Analysis for Predicting Outcome of Individual Breast Cancer Patients', Breast Cancer Res Tr 22, 285.
39. Ravdin, P., Clark, G., Hilsenbeck, S. et al. (1992), 'A Demonstration that Breast Cancer Recurrence can be Predicted by Neural Network Analysis', Breast Cancer Res Tr 21, 47.
40. Ravdin, P., McGuire, W. & Clark, G., U.S. Pat. No. 5,862,304, 'Method for predicting the future occurrence of clinically occult or non-existent medical conditions'.
41. Rehkugler, H. & Zimmerman, H. (1994) *Neuronale Netze in der Ökonomie* [Neural networks in the economy], Vahlen Verlag.
42. Ripley, B. (1993), 'Statistical Aspects of Neural Networks', in *Networks and Chaos—Statistical and Probabilistic Aspects*, eds. Barndorff-Nielsen, O., Jensen, J. & Kendall, W., Chapman & Hill.
43. Ritter, H., Martinetz, T. & Schulten, K. (1990), *Neuronale Netze, Eine Einführung in die Neuroinformatik Selbstorganisierender Netzwerke* [Neural networks, an introduction to the neuroinformatics of self-organizing networks], Addison-Wesley.
44. Royston, P. & Altman, D. (1994), 'Regression using fractional polynomials of continuous covariates, parsimonious parametric modelling', App. Stat. 43, 429.
45. Schumacher, M., Rossner, R. & Vach, W. (1996), 'Neural Networks and logistic regression', Computational Statistics and Data Analysis, 21, 661 (Part I).
46. Snow, P. B. et al. (1994), 'Artificial neural networks in the diagnosis and prognosis of prostate cancer, a pilot study', J Urol. November, 152(5 Pt 2), 1923.
47. Speight, P. M. et al. (1995), 'The use of artificial intelligence to identify people at risk of oral cancer and precancer', Br Dent J. November 25, 179(10), 382.
48. Tibshirani, R. (1996), 'A comparison of some error estimates for neural network procedures', Neural Computation 8, 152.
49. Tracey K. J. et al. (1992), 'Tumor necrosis factor in metabolism of disease, hormonal actions versus local tissue effects', Nouv Rev Fr Hematol., 34 Suppl, S37.
50. Tu, J. (1996), 'Advantages and Disadvantages of Using Artificial Neural Networks versus Logistic Regression for Predicting Medical Outcomes', J. Clin. Epidemiol. 49, 1225.
51. Warner, B. & Misra, M. (1996), 'Understanding neural networks as statistical tools', The American Statistician 50, 284.
52. Willoughby, T. R. et al. (1996), 'Evaluation and scoring of radiotherapy treatment plans using an artificial neural network', Int J Radiat Oncol Biol Phys. March 1, 34(4), 923.

What is claimed is:

1. A method for training a neural network in order to identify a patient risk function such that the structure of the neural network is simplified, wherein the neural network includes
   an input layer having a plurality of input neurons that receive input data,
   at least one intermediate layer having a plurality of intermediate neurons,
   an output layer having a plurality of output neurons that provide output signals, wherein the output signals define the patient risk function following a first occurrence of a disease on the basis of given training data records including objectifiable and metrologically captured data relating to the medical condition of a patient, and
   a multiplicity of synapses, wherein each said synapse interconnects a first neuron of a first layer with a second neuron of a second layer, defining a data sending and processing direction from the input layer toward the output layer,
wherein the method comprises:
   identifying and eliminating synapses of the multiplicity of synapses that have an influence on the curve of the risk function that is less than a predetermined significance including
   determining pre-change output signals of the neural network,
   selecting first and second sending neurons that are connected to the same receiving neuron by respective first and second synapses,
   assuming a correlation of response signals from said first and second sending neurons to the same receiving neuron,
   interrupting the first synapse and adapting in its place the weight of the second synapse,
   determining post-change output signals of the neural network,
   comparing the post-change output signals with the pre-change output signals, and
   eliminating the first synapse if the comparison result does not exceed a predetermined level.

2. The method of claim 1, wherein the first and second selected sending neurons are located on the same layer.

3. The method of claim 1, wherein interrupting the first synapse and adapting in its place the weight of the second synapse further includes adapting a value of a bias of the receiving neuron.

4. The method of claim 1, wherein identifying and eliminating synapses of the multiplicity of synapses that have an influence on the curve of the risk function that is less than a predetermined significance further includes
selecting a synapse, after determining the pre-change output signals of the neural network,
assuming that the selected synapse does not have a significant influence on the curve of the risk function,
interrupting the selected synapse, before determining the post-change output signals of the neural network and comparing the post-change output signals with the pre-change output signals, and
eliminating the selected synapse if the comparison result does not exceed the predetermined level.

5. The method of claim 4, further comprising
repeating the identifying and eliminating actions n times;
wherein comparing the post-change output signals with the pre-change output signals includes
comparing the post-change output signals with the pre-change output signals prior to performing the first identifying and eliminating actions, to provide a first comparison result; and
comparing the post-change output signals with the pre-change output signals after performing the n-1st identifying and eliminating actions, to provide a second comparison result;
wherein the comparison result is a cumulative comparison result including the first comparison result and the second comparison result.

6. The method of claim 1, further comprising
repeating the identify and eliminating actions n times;
wherein comparing the post-change output signals with the pre-change output signals includes
comparing the post-change output signals with the pre-change output signals prior to performing the first identifying and eliminating actions, to provide a first comparison result; and
comparing the post-change output signals with the pre-change output signals after performing the n-1st identifying and eliminating actions, to provide a second comparison result;
wherein the comparison result is a cumulative comparison result including the first comparison result and the second comparison result.

7. The method of claim 1, further comprising calculating a value of a likelihood function for the neural network to represent an expected output of the neural network.

8. The method of claim 1, further comprising comparing structure variants of the neural network using a significance test.

9. The method of claim 8, wherein the structure variants of the neural network are compared using a CHI-SQUARED test.

10. The method of claim 8, wherein the structure variants of the neural network are compared using a BOOT-STRAPPING method.

11. The method of claim 8, further comprising:
calculating a value of a likelihood function for the neural network;
wherein comparing structure variants of the neural network includes calculating a ratio of values of the likelihood functions for the structure variants.

12. The method of claim 1, further comprising optimizing strengths of connections between connected pairs of the neurons according to a simplex method.

13. A method for training a neural network in order to identify a patient risk function such that the structure of the neural network is simplified, wherein the neural network includes
an input layer having a plurality of input neurons that receive input data,
at least one intermediate layer having a plurality of intermediate neurons,
an output layer having a plurality of output neurons that provide output signals, wherein the output signals define the patient risk function following a first occurrence of a disease on the basis of given training data records including objectifiable and metrologically captured data relating to the medical condition of a patient, and
a multiplicity of synapses, wherein each said synapse interconnects a first neuron of a first layer with a second neuron of a second layer, defining a data sending and processing direction from the input layer toward the output layer,
wherein the method comprise:
identifying and eliminating synapses of the multiplicity of synapses that have an influence on the curve of the risk function that is less than a predetermined significance, including
determining pre-change output signals of the neural network,
selecting a synapse,
assuming that the selected synapse does not have a significant influence on the curve of the risk function,
interrupting the selected synapse,
determining posts-change output signals of the neural network,
comparing the post-change output signals with the pro-change output signals, and
eliminating the selected synapse if the comparison result does not exceed a predetermined level.

14. The method of claim 13, further comprising
repeating the identifying and eliminating actions n times;
wherein comparing the post-change output signals with the pre-change output signals includes
comparing the post-change output signals with the pre-change output signals prior to performing the first identifying and eliminating actions, to provide a first comparison result; and
comparing the post-change output signals with the pre-change output signals after performing the n-1st identifying and eliminating actions, to provide a second comparison result;
wherein the comparison result is a cumulative comparison result including the first comparison result and the second comparison result.

* * * * *